United States Patent [19]

Adams

[11] Patent Number: 4,801,837
[45] Date of Patent: Jan. 31, 1989

[54] PIEZOELECTRIC LOAD MEASUREMENT APPARATUS AND CIRCUITS

[76] Inventor: Tello Adams, 8400 141st St., Seminole, Fla. 33542

[21] Appl. No.: 130,179

[22] Filed: Dec. 8, 1987

Related U.S. Application Data

[63] Continuation-in-part of Ser. No. 001,901, Jan. 9, 1987, and a continuation-in-part of Ser. No. 029,233, Mar. 3, 1987.

[51] Int. Cl.$^4$ ............................................. H01L 41/08
[52] U.S. Cl. ................................. 310/316; 310/319; 310/321; 310/338
[58] Field of Search ............... 310/316, 317, 321–325, 310/338; 318/116; 73/700, 702, 12, 88, 23, 432 PS, 580, 170 R, 703, 706; 177/210 FP; 340/619–621; 324/61 P, 61 QS

[56] References Cited

U.S. PATENT DOCUMENTS

| | | | |
|---|---|---|---|
| 3,191,913 | 6/1965 | Mettler | 310/317 X |
| 3,253,219 | 5/1966 | Littler | 310/321 X |
| 3,371,233 | 2/1968 | Cook | 310/317 |
| 3,879,992 | 4/1975 | Bartera | 310/321 X |
| 4,239,088 | 12/1980 | Check et al. | 310/338 X |
| 4,277,758 | 7/1981 | Mishiro | 310/316 X |
| 4,294,105 | 10/1981 | Kelly | 310/321 X |
| 4,485,323 | 11/1984 | Corbett | 310/321 X |
| 4,561,286 | 12/1985 | Sekler et al. | 310/321 X |
| 4,656,383 | 4/1987 | Alibert | 310/321 X |
| 4,721,874 | 1/1988 | Emmert | 310/316 X |
| 4,727,277 | 2/1988 | Adams | 310/316 X |
| 4,734,609 | 3/1988 | Jasmine | 310/338 X |

Primary Examiner—Mark O. Budd

[57] ABSTRACT

An oscillator employs a single flat piezo-electric transducer as a frequency determining element. The transducer has first, second and third mutually orthogonal axes. The first and second axes lie in a selected one of first and second planes. The first plane is the plane of the transducer, the second plane is at right angles to the first plane. The third axis is perpendicular to the selected plane. The transducer has different modes of excitation in different planes which have different resonant frequencies. The oscillator has a positive feedback loop containing in series a high pass filter and a low pass filter which together [a] determine one selected mode of excitation of the transducer in the selected plane with an associated resonant frequency whereby the transducer resonates in the selected plane at the associated resonant frequency and [b] also prevent the transducer from being excited along the third axis. The transducer yields thereacross an oscillatory voltage having a predetermined maximum peak to peak voltage value in the absence to any load exerted upon the transducer. When a load directed along the third axis is applied to the transducer, the voltage value increases as the magnitude of the load decreases and decreases as the magnitude of the load increases.

3 Claims, 1 Drawing Sheet

PIEZOELECTRIC LOAD MEASUREMENT APPARATUS AND CIRCUITS

CROSS REFERENCE TO COPENDING APPLICATIONS

The present application is a continuation-in-part of copending applications Ser. No. 001,901, filed on Jan. 9, 1987 and Ser. No. 029,233, filed Mar. 3, 1987.

BACKGROUND OF THE INVENTION

Use of oscillators employing piezo-electric transducers as frequency determining elements in applications for detecting the presence or absence of materials is well known, as for example, detecting the presence or absence of frost on cooling fins of refrigerators, as shown in U.S. Pat. No. 4,176,524, or the presence or absence of liquid, as shown in U.S. Pat. No. 4,019,072. In devices of this type, the oscillator has a steady state condition of operation when the transducer is not subject to load, as for example the absence of the material being detected, and ceases to oscillate when the material is present and applies a load to the transducer. More particularly, the transducer ceases to resonate when subjected to any type of damping or loading. As a result, the transducer can be used to measure qualitative changes, such as the presence or absence of material, but cannot be used to measure quantitative changes such as changes in the thickness of frost or changes in liquid levels.

In contradistinction, the present invention is directed toward measuring devices using oscillators employing piezo-electric transducers which can be used to measure quantitative changes of the character indicated.

SUMMARY OF THE INVENTION

It is a characteristic of the prior art devices described above that transducer loading and transducer resonance take place in the same plane. In the present invention, transducer loading and transducer resonance take place in quadrature, as for example in planes and axes at right angles to each other. Under these conditions, variable load damping can be used to produce different resonance conditions.

In accordance with the principles of the invention, load measurement apparatus utilizes an oscillator employing a single flat piezo-electric transducer as a frequency determining element.

The transducer has first, second and third mutually orthagonal axes, the first and second axes lying in a selected one of first and second planes. The third axis is perpendicular to the selected plane. The first plane is the plane of the transducer. The second plane is perpendicular to the first plane. The transducer has different modes of excitation in different planes which have different resonant frequencies.

The oscillator has a positive feedback loop containing in series a high pass filter and a low pass filter which together [a] determine one selected mode of excitation of the transducer in the selected one of the first and second planes with an associated resonant frequency whereby the transducer resonates in the selected plane at the associated resonant frequency and [b] also prevent the transducer from being excited along the third axis. The transducer yields thereacross an oscillatory voltage having a predetermined maximum peak to peak voltage value in the absence of any load exerted upon the transducer.

When a load directed along the third axis is applied to the transducer, the peak to peak value of the oscillatory voltage decreases from the maximum as the magnitude of the load increases and increases toward the maximum as the magnitude of the load decreases whereby the value is a monatonic function of the magnitude of the load.

DETAILED DESCRIPTION OF PREFERRED EMBODIMENTS

Figure 1:
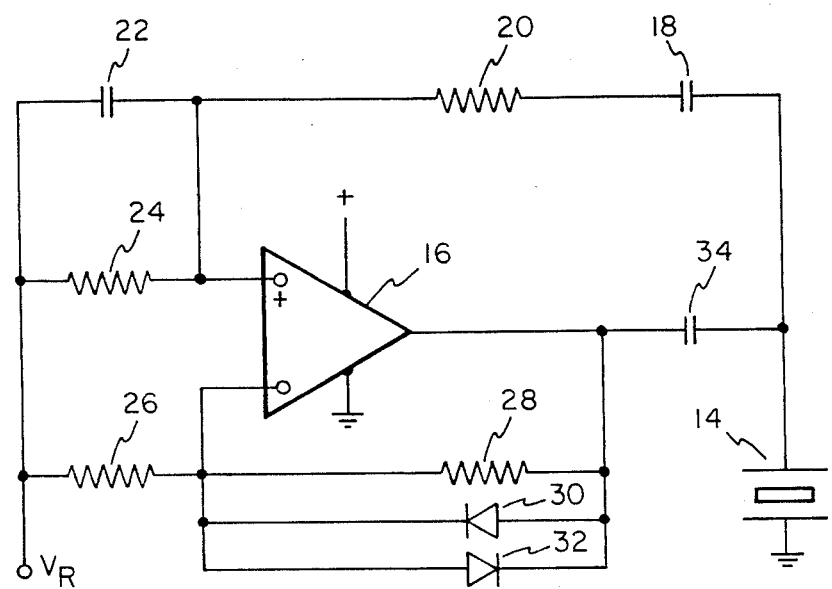
FIG. 1 is a circuit diagram of an oscillator incorporating a piezo-electric transducer wherein transducer excitation and resonance are in quadrature.
Figures 2, 3:
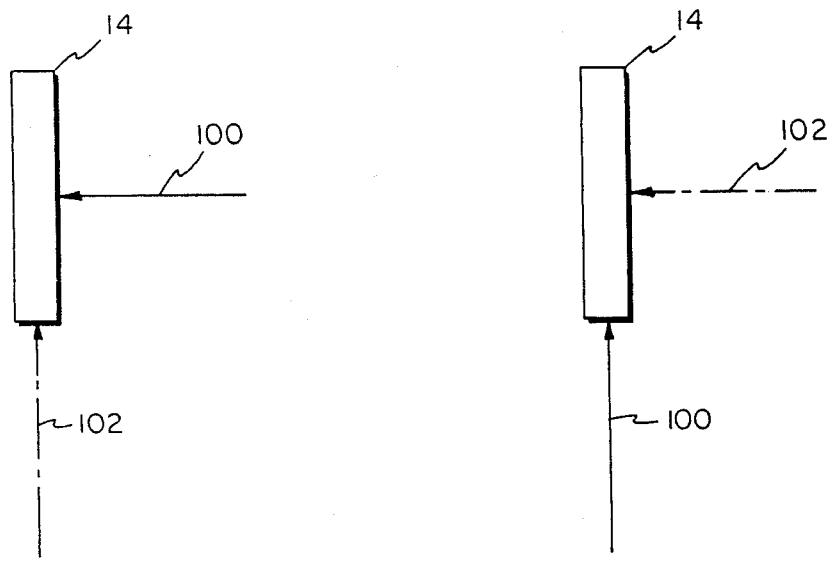
FIG. 2 illustrates one direction of loading which can be used with the oscillator circuit of FIG. 1.
FIG. 3 illustrates another direction of loading which can be used with the oscillator circuit of FIG. 1.

Referring now to FIGS. 1–3, the piezo-electric transducer 14 is a thin flat element, as for example a disc having a diameter of 0.25 inches and a thickness of 0.08 inches. Transducers, depending upon their geometry, have different frequencies which differ, depending upon the mode of operation. In a lower range of resonant frequencies [in this particular example, the selected resonant frequency is within this lower range and is about 320 kilohertz], transducer 14 can resonate in the radial mode, across the disc, whereby the amplitude excursions of the disc cause it to elongate and contract in the plane of the disc. This plane is the first or X-Y plane. In a higher range of resonant frequencies, the transducer can resonate in the axial mode, through the disc, whereby the amplitude excursions of the disc cause it to elongate and contract in another plane which is perpendicular to the plane of the disc. This plane is the second or Z-Y or Z-X plane.

The circuit of FIG. 1 can be used to cause the transducer to resonate in either the first or second plane. An operational amplifier 16 utilizes a positive feedback loop including a high pass filter formed by capacitor 18 and resistor 20 and a low pass filter formed by resistor 20 and capacitor 22. These filters are in series, the bottom frequency of the high pass filter being essentially the same as the top frequency of the low pass filter. These frequencies are essentially the same as the selected resonant frequency of the transducer and enable the transducer to oscillate in the desired mode while at the same time preventing oscillation in undesired modes. Resistor 24 is used to set the operating bias point of the amplifier 16. Diodes 30 and 32 set the range of the amplitude of the oscillations and the range of the amplitude excursion of the transducer. Capacitor 34 determines the drive level to the transducer, and, to some extent, the phase, while resistors 26 and 28 control the masimum loop gain.

When the filters are set for radial mode resonance, and as shown in FIG. 2, a load identified in solid line 100 such as a pressure is directed at right angles to the X-Y plane in a direction along the Z axis and lying in either the Z-X or Z-Y plane, the peak to peak value of the oscillatory voltage developed across the transducer decreases from the maximum zero or no load value maintained by the diodes 30 and 32 as the magnitude of the load increases and increases toward the maximum as the magnitude of the load decreases whereby the value is a monatonic function of the magnitude of the load. This value can be reduced substantially as for example to about 3½ (0.7 Vpp) percent of the maximum value before the loading can be increased to such magnitude that oscillations cease. In contradistinction, when a load which only slightly reduces the value of peak to peak voltage is applied as shown in dotted line 102 to the transducer along the X or Y axis or any other direction in the plane of the transducer, oscillations immediately cease.

As shown in FIG. 3, when the filters are set for axial mode resonance, the same monatonic function is established when the solid line of loading 100 is directed in along a direction at right angles to the Z axis and lying in the X-Y plane and, moreover, oscillations cease when the dotted line of loading is directed along the Z axis in either the Z-X or Z-Y plane.

What is claimed is:

1. Load measurement apparatus comprising:
    an oscillator employing a single flat piezo-electric transducer as a frequency determining element, the transducer having first, second and third mutually orthagonal axes, the first and second axes lying in a selected one of first and second planes, the first plane being the plane of the transducer, fthe second plane being at right angles to the first plane, the third axis being perpendicular to the selected plane, the transducer having different modes of excitation in different planes at different resonant frequencies, the oscillator having a positive feedback loop containing in series a high pass filter and a low pass filter which together [a] determine one selected mode of excitation of the transducer in said selected plane with an associated resonant frequency whereby the transducer resonates in the selected plane at the associated resonant frequency and [b] prevent the transducer from being excited along the third axis, the transducer yielding thereacross an oscillatory voltage having a predetermined maximum peak to peak voltage value in the absence ot any load exerted upon the transducer; and
    means to apply a load to the transducer which is directed along the third axis, said peak to peak voltage value increasing toward the maximum as the magnitude of the load decreases and decreasing away from the maximum as the magnitude of the load increases whereby the peak to peak voltage value is a monatonic function of the magnitude of the load.

2. Apparatus as set forth in claim 1 wherein the first and second axes lie in the first plane.

3. Apparatus as set forth in claim 1 wherein the first and second axes lie in the second plane.

* * * * *